United States Patent
Rui et al.

(10) Patent No.: US 10,779,778 B2
(45) Date of Patent: *Sep. 22, 2020

(54) REFERENCE DETECTOR ELEMENTS IN CONJUNCTION WITH AN ANTI-SCATTER COLLIMATOR

(71) Applicant: General Electric Company, Schenectady, NY (US)

(72) Inventors: Xue Rui, Clifton Park, NY (US); Geng Fu, Rexford, NY (US); Yannan Jin, Schenectady, NY (US); Jianjun Guo, Ballston Spa, NY (US); Peter Michael Edic, Albany, NY (US); Brian David Yanoff, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 562 days.

This patent is subject to a terminal disclaimer.

(21) Appl. No.: 15/589,412

(22) Filed: May 8, 2017

(65) Prior Publication Data
US 2018/0317869 A1    Nov. 8, 2018

(51) Int. Cl.
*A61B 6/00* (2006.01)
*A61B 6/06* (2006.01)
*G21K 1/02* (2006.01)
*G01T 1/29* (2006.01)

(52) U.S. Cl.
CPC .............. *A61B 6/4291* (2013.01); *A61B 6/06* (2013.01); *A61B 6/4233* (2013.01); *A61B 6/5205* (2013.01); *A61B 6/585* (2013.01); *G01T 1/2928* (2013.01); *G21K 1/025* (2013.01); *A61B 6/5282* (2013.01)

(58) Field of Classification Search
CPC ......... A61B 6/032; A61B 6/06; A61B 6/4241; A61B 6/4291; A61B 6/461; A61B 6/5205; A61B 6/54; A61B 6/585; A61B 6/4233; A61B 6/5282; G01T 1/244; G01T 1/2907; G01T 1/2928; G21K 1/025
See application file for complete search history.

(56) References Cited

U.S. PATENT DOCUMENTS

| | | | |
|---|---|---|---|
| 4,982,096 A * | 1/1991 | Fujii | ..................... G01T 1/2018 250/366 |
| 7,486,764 B2 | 2/2009 | Tkaczyk et al. | |
| 7,564,940 B2 | 7/2009 | Mattson et al. | |
| 9,219,178 B2 | 12/2015 | Zhang et al. | |
| 10,222,489 B2 * | 3/2019 | Fu | ........................... G01T 1/247 |
| 2004/0008810 A1 | 1/2004 | Nelson et al. | |

(Continued)

OTHER PUBLICATIONS

Donald, Carolyn A., et al.; Direct Digital Mammography Using Capillary Optics, Medicine and Medical Research Optics, Jul. 1999.

(Continued)

*Primary Examiner* — Chih-Cheng Kao

(57) ABSTRACT

The present approach relates to the use of detector elements (i.e., reference detector pixels) positioned under septa of an anti-scatter collimator. Signals detected by the reference detector pixels may be used to correct for charging-sharing events with adjacent pixels and/or to characterize or correct for focal spot misalignment either in real time or as a calibration step.

19 Claims, 15 Drawing Sheets

(56) References Cited

U.S. PATENT DOCUMENTS

| | | | |
|---|---|---|---|
| 2006/0182228 A1* | 8/2006 | Toth | A61B 6/032 |
| | | | 378/205 |
| 2006/0284097 A1* | 12/2006 | Wang | G01T 1/1611 |
| | | | 250/363.04 |
| 2007/0206721 A1 | 9/2007 | Tkaczyk et al. | |
| 2008/0061395 A1 | 3/2008 | Tkaczyk et al. | |
| 2012/0232385 A1* | 9/2012 | Hattori | G01T 1/1648 |
| | | | 600/436 |
| 2014/0341333 A1 | 11/2014 | Wang et al. | |
| 2016/0169737 A1* | 6/2016 | Bouhnik | G01T 1/1647 |
| | | | 250/208.1 |

OTHER PUBLICATIONS

Del Sordo, Stefano, et al.; Progress in the Development of CdTe and CdZnTe Semiconductor Radiation Detectors for Astrophysical and Medical Applications, National Center for Biotechnology Information, vol. 9, Issue 5, pp. 3491-3526, May 12, 2009.

Li, Liang, et al.; Geometric Estimation Method for X-Ray Digital Intraoral Tom synthesis, Society of Photo-Optical Instrumentation Engineers, Jun. 2016.

\* cited by examiner

REFERENCE DETECTOR ELEMENTS IN CONJUNCTION WITH AN ANTI-SCATTER COLLIMATOR

BACKGROUND

The subject matter disclosed herein relates to the use of detectors employing an anti-scatter grid, including semiconductor-based detectors.

Non-invasive imaging technologies allow images of the internal structures or features of a subject (patient, manufactured good, baggage, package, or passenger) to be obtained non-invasively. In particular, such non-invasive imaging technologies rely on various physical principles, such as the differential transmission of X-ray photons through the target volume or the reflection of acoustic waves, to acquire data and to construct images or otherwise represent the internal features of the subject.

For example, in X-ray-based imaging technologies, X-ray radiation spans a subject of interest, such as a human patient, and a portion of the radiation impacts a detector where the intensity data is collected. In digital X-ray systems, a detector produces signals representative of the amount or intensity of radiation impacting discrete pixel regions of a detector surface. The signals may then be processed to generate an image that may be displayed for review.

In one such X-ray-based technique, known as computed tomography (CT), a scanner may project fan-shaped or cone-shaped X-ray beams from an X-ray source at numerous view angle positions about an object being imaged, such as a patient. The X-ray beams are attenuated as they traverse the object and are detected by a set of detector elements which produce signals representing the intensity of the incident X-ray intensity on the detector. The signals are processed to produce data representing the line integrals of the linear attenuation coefficients of the object along the X-ray paths. These signals are typically called "projection data" or just "projections". By using reconstruction techniques, such as filtered backprojection, images may be generated that represent a volume or a volumetric rendering of a region of interest of the patient or imaged object. In a medical context, pathologies or other structures of interest may then be located or identified from the reconstructed images or rendered volume.

Radiation detectors used in these types of imaging techniques may operate in an energy-integrating mode (i.e., readout of the total integrated energy deposited during an acquisition interval) or a photon-counting mode (each individual X-ray photon is detected and counted). Energy integration is the conventional mode for X-ray detectors in most clinical applications. However, photon-counting detectors offer other benefits relative to energy-integrating detectors, such as improved resolution, the ability to improve contrast-to-noise ratio, the ability to better delineate materials in the X-ray beam, and so on.

In many instances an anti-scatter grid (e.g., a collimator) may be employed near or on the surface of the detector that faces the radiation source. The anti-scatter grid may be useful in reducing or eliminating the effects of X-ray photons that have not traveled in a straight path to the detector, such as due to being scattered by objects. However, a consequence of the presence of such an anti-scatter grid is a loss of available detection surface of the detector in those portions of the detector underlying the anti-scatter grid.

BRIEF DESCRIPTION

In one embodiment, a radiation detector is provided. In accordance with this embodiment, the radiation detector includes an anti-scatter collimator comprising X-ray attenuating septa arranged in a one-dimensional or two-dimensional geometry and a radiation detector panel. The radiation detector panel includes an array of primary pixels positioned so as to not be beneath the septa of the anti-scatter collimator and at least one reference pixel adjacent one or more respective primary pixels and positioned beneath a respective septum or intersection of septa.

In a further embodiment, a method for measuring the position of an X-ray focal spot relative to a detector is provided. In accordance with this embodiment, signals read out from one or more reference pixels of a detector panel are analyzed for a signal pattern. The one or more reference pixels are positioned beneath X-ray attenuating septa or septa intersections of an anti-scatter collimator positioned proximate to the detector panel. If no signal pattern is detected, no corrective action is taken. If a signal pattern is detected, an X-ray focal spot position is estimated based on the signal pattern.

In an additional embodiment, an imaging system is provided. In accordance with this embodiment, the imaging system includes an X-ray source configured to emit X-ray photons from a focal spot during operation and a radiation detector assembly. The radiation detector assembly includes an anti-scatter collimator comprising X-ray attenuating septa and a radiation detector panel. The radiation detector panel includes an array of primary pixels positioned so as to not be beneath the septa of the anti-scatter collimator and one or more reference pixels positioned beneath respective septa or intersections of septa. The imaging system further includes readout electronics configured to combine a signal from the one or more reference pixels and a respective primary pixel when a charge-sharing event occurs.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
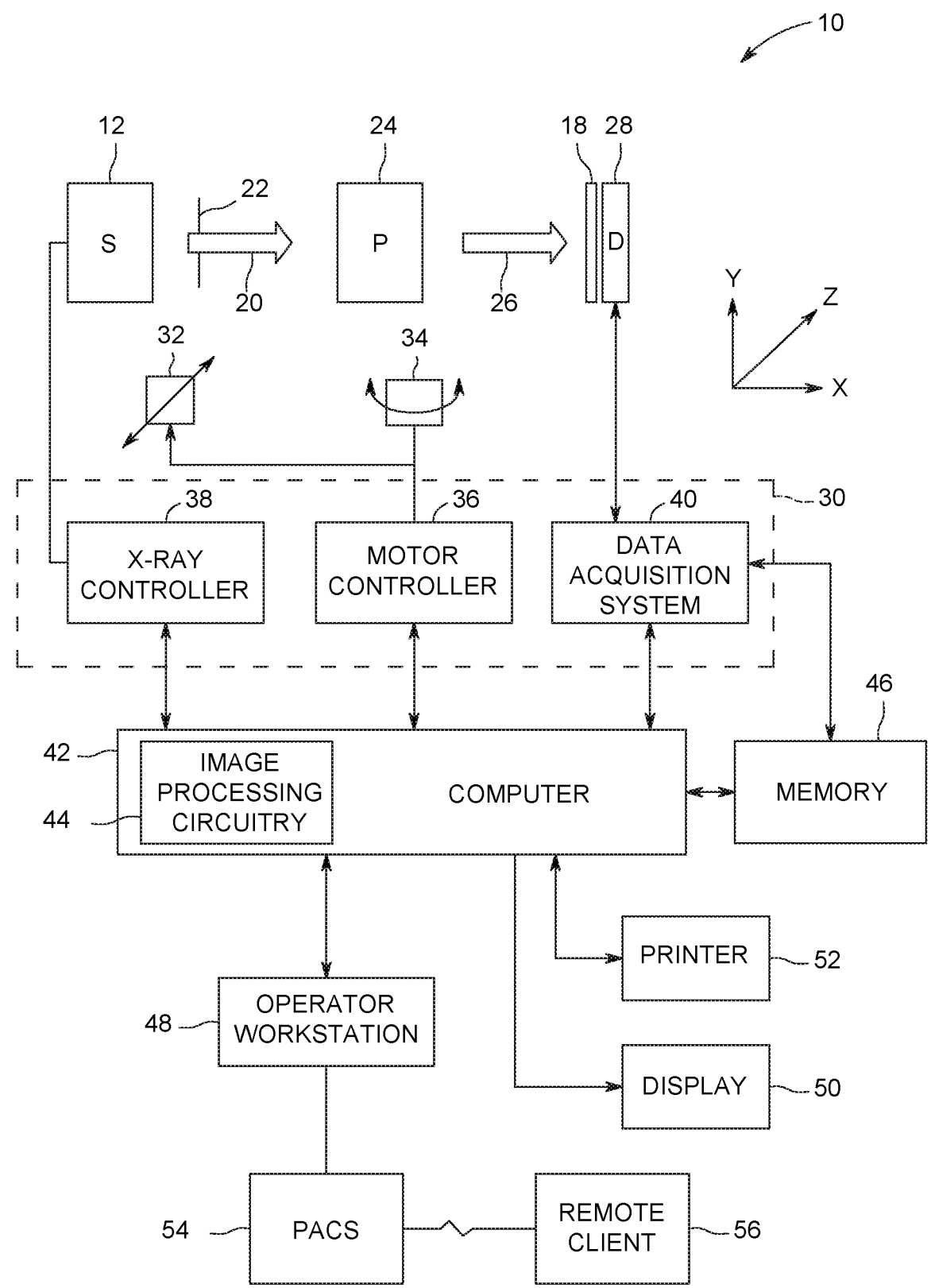
FIG. 1 is a schematic illustration of an embodiment of a computed tomography (CT) system configured to acquire CT images of a patient and process the images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality-control or quality-review applications), and/or the non-invasive inspection of packages, boxes, luggage, and so forth (i.e., security or screening applications). In general, the present approaches may be desirable in any imaging or screening context in which energy discrimination in a photon-counting context is desirable.

As discussed herein, the present approach relates to the use of detector cells or elements (i.e., reference detector cells or pixels) that are present below the septa of an anti-scatter collimator, which may be formed as a grid. Such an approach, as discussed herein, allow the reference detector cells, which are typically not directly illuminated by X-ray photons, to be employed to correct for charge-sharing events from neighboring primary (i.e., illuminated) pixels for direct-conversion detectors, also referred to as active or readout pixels herein. That is, since the reference detector is under the collimator, the primary signal is blocked. Thus, the signal detected by the reference detector mostly comes from charge sharing events which may be attributed to a neighboring, primary or illuminated pixel. In this manner a radiation detector, such as a room-temperature semiconductor (e.g., silicon-based, cadmium telluride-based, and so forth) detector operating using direct-conversion principles, may generate reference signals to supplement the signals generated by primary detection events.

In addition, due to being in the shadow of the collimator, the signal from the reference detector cell is sensitive to relative motion between the focal spot and the detector. That is, movement or wobble of the focal spot relative to the reference detector cell may determine whether the collimator blocks an X-ray photon or not. As discussed herein, this sensitivity to relative motion can be used to calibrate the relative position of the collimator and the source, or to adjust the position of the focal spot in real-time based on direct feedback of the signals from the reference detector cell(s).

With the preceding discussion in mind, FIG. 1 illustrates an embodiment of an imaging system 10 for acquiring and processing image data using reference detector cells situated beneath the septa of an anti-scatter gird or collimator in accordance with structures and approaches discussed herein. In the illustrated embodiment, system 10 is a computed tomography (CT) system designed to acquire X-ray projection data and to reconstruct the projection data into volumetric reconstructions for display and analysis. The CT imaging system 10 includes one or more X-ray sources 12, such as one or more X-ray tubes or solid state emission structures which allow X-ray generation at one or more energy spectra during an imaging session.

In certain implementations, the source 12 may be positioned proximate to a filter assembly or beam shaper 22 that may be used to steer the X-ray beam 20, to define the shape and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry, between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-ray photons 20, resulting in attenuated X-ray photons 26 that impinge upon a detector array 28 formed by a plurality of detector elements (e.g., pixels) as discussed herein. The detector 28 may be an energy-integrating detector, a photon-counting detector, an energy-discriminating detector, or any other suitable radiation detector. By way of example, the detector 28 may be an energy-discriminating photon-counting detector, whose outputs convey information about the number and energy of photons that impact the detector at measured positions and over a time interval corresponding to a scan or imaging session. In one embodiment, the detector 28 may be a direct-conversion type detector (i.e., a detector that does not employ a scintillator intermediary), such as a detector based on silicon strips or other semiconductor materials that generate a measurable signal when the semiconductor sensor is itself exposed to X-ray photons.

In the depicted example, the detector 28 is adjacent or otherwise proximate to an anti-scatter collimator 18 that is typically made of a material that absorbs or otherwise blocks X-ray photons. Thus, X-ray photons striking the septa of the anti-scatter collimator 18, after being reflected or deflected by the object 24, or otherwise moving at an angle relative to the septa of the anti-scatter collimator 18, are prevented from reaching the detector 28. Conversely, X-ray photons traveling in a relatively straight path from the X-ray source 12 to the detector 28 are unimpeded by the anti-scatter collimator 18 and reach the detector 28. A small percentage of these photons strike and are attenuated by the cross section of the anti-scatter collimator. For the purpose of discussion herein, the detector 28 may in certain instances be referred to as being beneath or in the "shadow" of the anti-scatter collimator 18 as seen from the perspective of the X-ray source 12. Such characterization denotes a relationship in which the collimator 18 is always between the X-ray source 12 and detector 28 and the X-ray source 12 is viewed (regardless of actual orientation or position) as being "up" and a source of X-ray illumination. As will be appreciated, however, such characterization does not necessarily denote absolute position or orientation information.

With respect to the detector 28, as discussed herein the detector 28 typically defines an array of detector elements, each of which produces an electrical signal when exposed to X-ray photons. The electrical signals are acquired and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols, and may process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move the subject 24 and/or components of the imaging system 10, respectively. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal spot size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the detector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data (e.g., soft tissue images, bone images, segmented vascular trees, and so on), material basis images, and/or material decomposition results, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

With the preceding discussion of an overall imaging system 10 in mind, the present approaches utilize signals measured from beneath the anti-scatter collimator 18 for various purposes, such as charge-sharing and/or focal spot corrections. This contrasts with prior techniques in which the detector regions (e.g., pixels) beneath the anti-scatter collimator 18 where de-activated or otherwise not read out or utilized.

Figure 2:
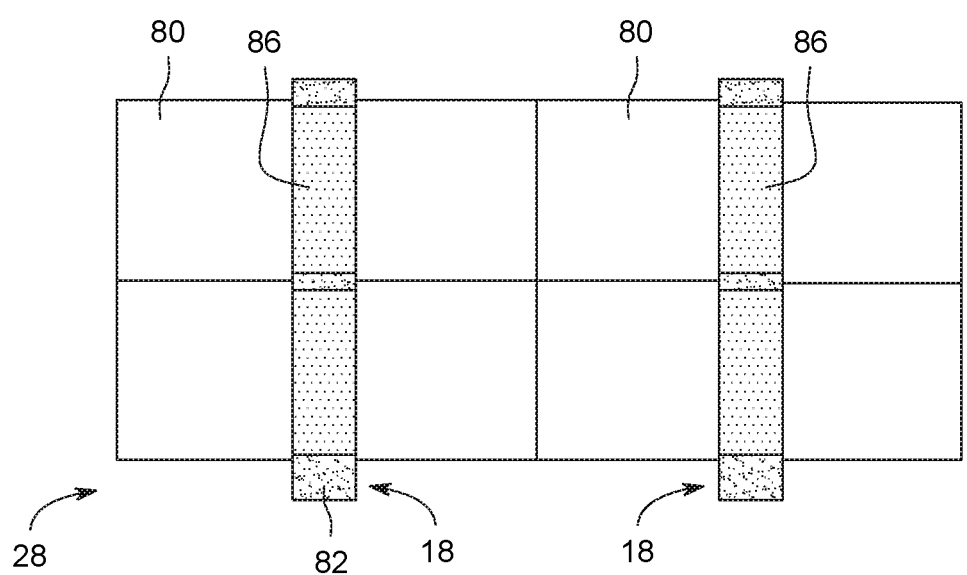
FIG. 2 is a top view of a one-dimensional (1D) anti-scatter collimator and detector arrangement with reference detector pixels positioned under the anti-scatter collimator, in accordance with aspects of the present approach.
Figure 3:
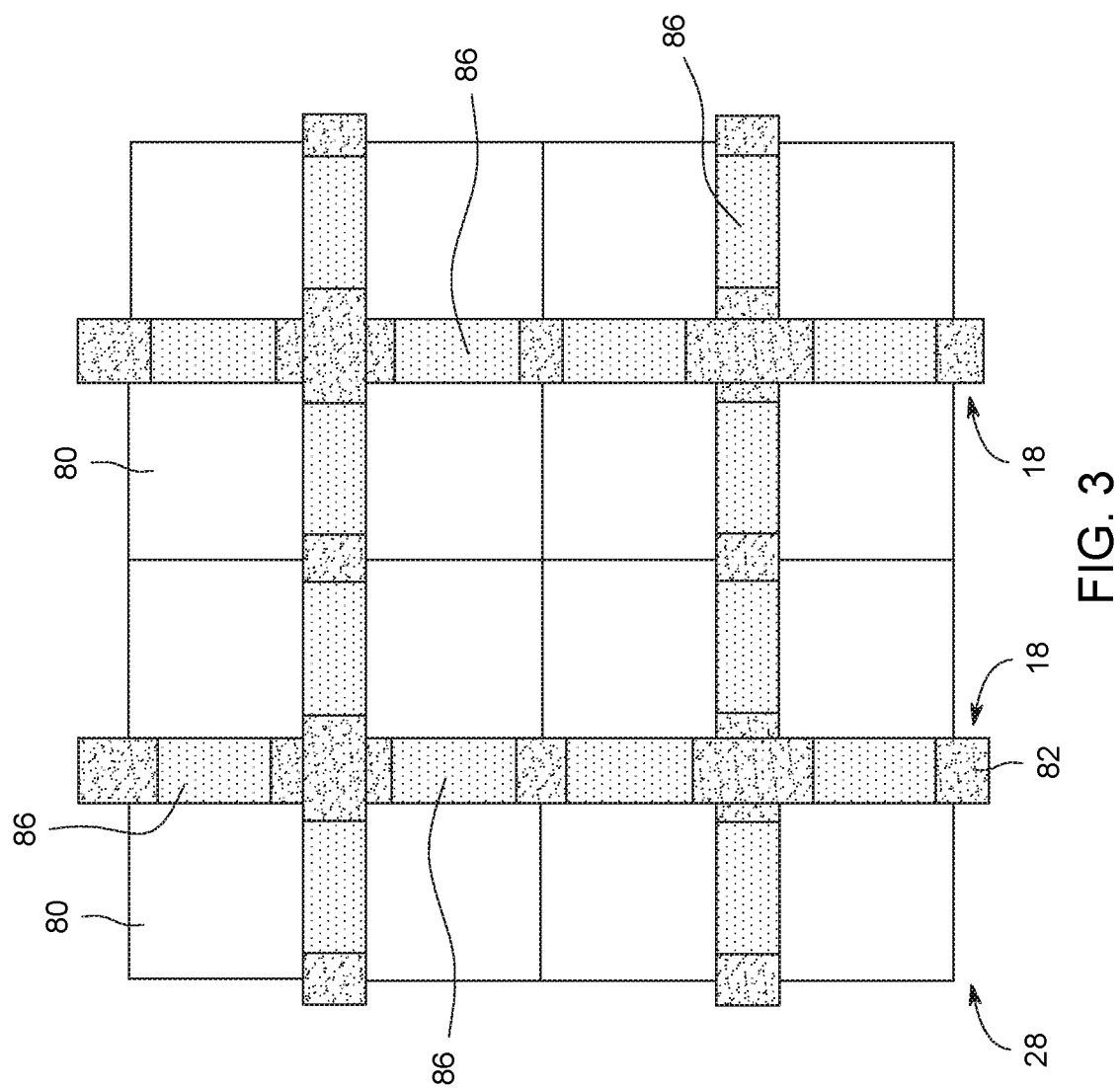
FIG. 3 is a top view of a two-dimensional (2D) anti-scatter collimator and detector arrangement with reference detector pixels positioned under the anti-scatter collimator, in accordance with aspects of the present approach.

In the present approach, the detector elements (e.g., pixels) beneath the area corresponding to the anti-scatter grid septa are denoted as reference detectors having corresponding detector elements or pixels. This is conceptually illustrated for a one-dimensional (1D) anti-scatter collimator 18 (FIG. 2) and a two-dimensional (2D) anti-scatter collimator 18 (FIG. 3). In these examples, an array of primary (i.e., active or readout) pixels 80 (e.g., a 500 µm×500 µm pixel or 1 mm×1 mm pixel) of a detector 28 is defined. The primary pixels are those pixels used to generate projection data that are processed to generate images as part of a scan. An anti-scatter collimator 18 defined by a plurality of septa 82 is provided adjacent or otherwise proximate (e.g., over) the detector 28. The area of the detector 28 under the septa 82 is generally shielded from incident X-ray photons.

In these examples, however, a reference detector pixel 86 (i.e., reference detector) is provided beneath the septa (82) adjacent each primary pixel 80. As the septa of the anti-scatter grid have a relatively narrow cross-sectional area relative to the primary pixel area, so as to maximize useful signal, the area of the reference detector pixels is less than the corresponding primary pixel area.

The signals from the reference detector pixels 86 and the primary pixels 80 may be read out separately, such as using separate readout circuitry (e.g., application specific integrated circuits—ASICs) of the detector panel and/or of the DAS, or may be read out using the same readout circuitry and separately processed based on control logic. For certain operations discussed herein, such as the combination or summing of signals read from reference detector pixels with the signals of primary pixels, such combining or summing functionality may be provided on the readout circuitry or ASIC(s). Signal read out from the reference pixels 86 may be used for various purposes, as discussed herein. By way of example, the signal from the reference pixels 86 may be used for one or both of focal spot motion detection/correction or charge-sharing correction.

Figure 4:
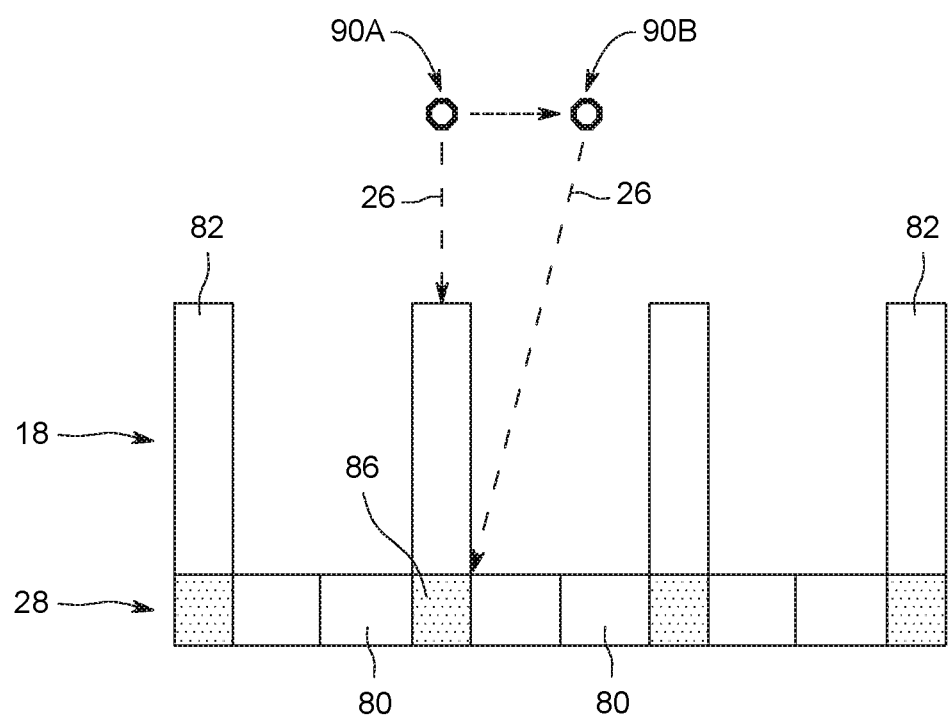
FIG. 4 is a side view of an anti-scatter collimator and detector arrangement with reference detector pixels positioned under the anti-scatter collimator and showing focal spot alignment and misalignment, in accordance with aspects of the present approach.

By way of example, and turning to FIG. 4, a side view of a detector 28 with reference pixels 86 underlying septa 82 of an anti-scatter collimator 18 is depicted. In this example, a focal spot corresponding to X-ray emission from the X-ray source 12 is depicted in an aligned position (focal spot 90A) and unaligned position (focal spot 90B). With respect to such focal spot motion, for certain imaging systems, the focal spot position may move in the x dimension (i.e., laterally) by ±25 µm and/or in the z dimension (i.e., longitudinally) by 150 µm or more, such as a function of X-ray tube temperature. It may be noted that unalignment or misalignment of the focal spot 90 may be unintentional, such as due to a lack of current calibration of the system, or intentional, such as due to the use of scanning approaches employing focal spot wobble at the X-ray source for improved projection data sampling.

As shown in FIG. 4, when the focal spot is in the aligned position the X-ray photons 26 are blocked by the septa 82 of the anti-scatter collimator 18 from reaching the reference detector pixels 86, and therefore will not generate a signal. Conversely, when the focal spot is offset from alignment, the X-ray photons 26 are able to reach the reference detector pixels 86 and will generate a signal in response to incident X-ray photons 26. In this manner, signals generated by the reference detector pixels 86 can be used to track the movement of the focal spot during a scan, allowing an adjustment factor (or factors) to be calculated for focal spot position during the scan, which may then be used by the reconstruction algorithm. Such adjustment factors may correspond to a geometric correction factor that compensates for a misalignment of the focal spot during a scan.

For example, the pattern of the reference detector signal during an air scan can be used to calibrate the motion of the focal spot 90. Such calibration may take the form of applying a calibration or correction factor to signals acquired during a scan to compensate for the measured focal spot misalignment.

In another approach, the pattern of the reference detector signal observed at the edge of the detector 28 can be used to capture the relative position or motion of the focal spot 90 during a scan operation, assuming the reference detector pixels 86 at the edge of the detector 28 are not totally blocked by the object or patient being scanned. In one such approach, tracked focal spot position may be used to calculate a correction or adjustment that compensates for focal spot misalignment in the reconstruction algorithm (i.e., provided a corrected focal spot position for reconstruction purposes).

Figure 5:
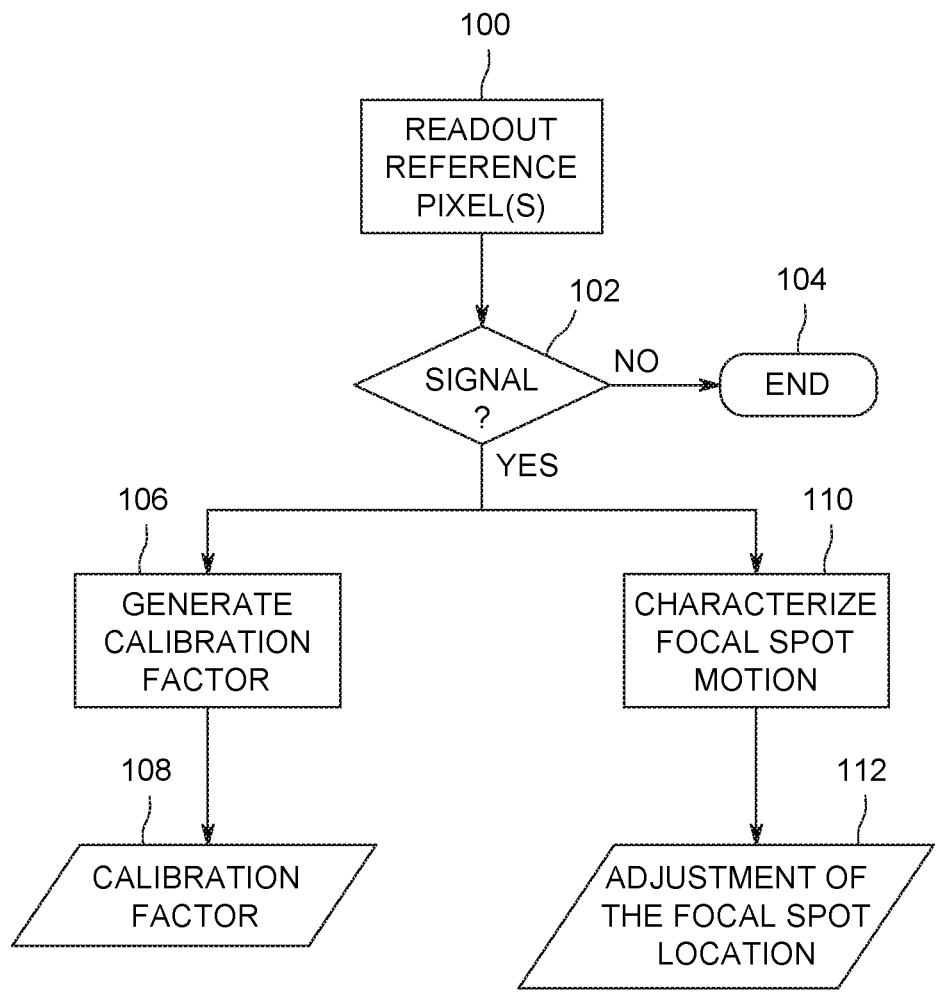
FIG. 5 depicts a process flow for performing focal spot calibration and/or focal spot position adjustment using reference detector signals, in accordance with aspects of the present approach.

The above approaches are illustrated as a process flow in FIG. 5. In the depicted flow, one or more reference pixels 86 are read out (block 100). If no signal is detected (decision block 102), the process is terminated (block 104). Depending on the operation, if a signal is detected at block 102 a calibration factor 108 may be generated (block 106) (such as during an air scan performed as part of a calibration process) or one or more scan-based focal spot location adjustments 112 may be derived that characterize focal spot motion (block 110) during an examination procedure and which can be used to adjust the focal spot position for reconstruction process. Alternatively, the focal spot adjustments 112 may be used during a scan for real-time modification of the focal spot location as the scan is being performed.

Figure 6:
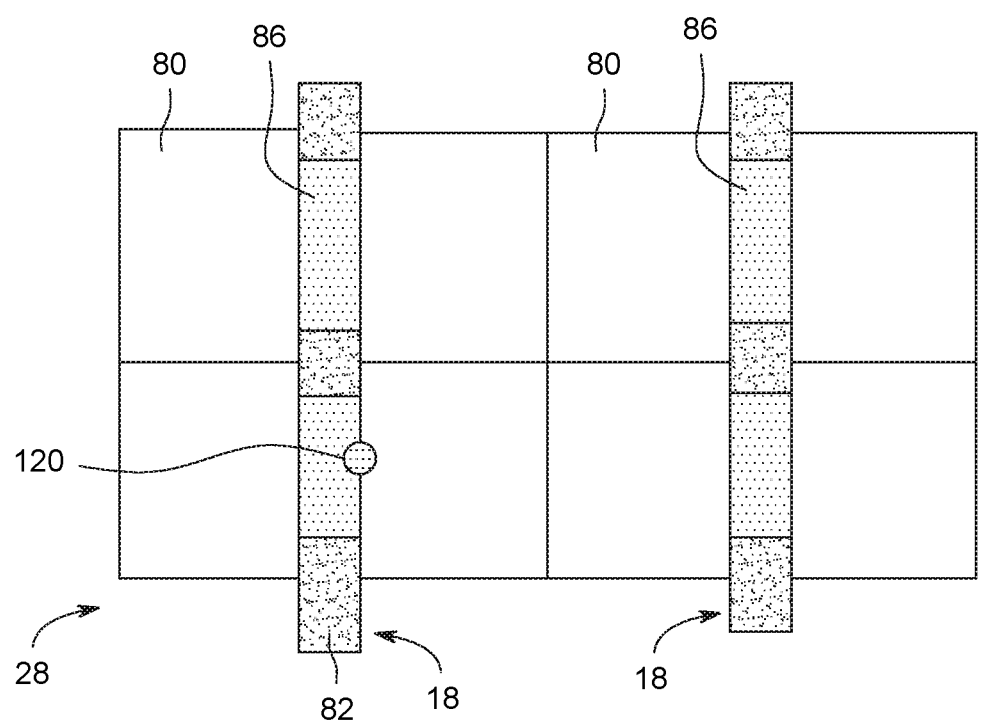
FIG. 6 is a top view of a charge-sharing event in the context of the anti-scatter collimator and detector arrangement of FIG. 2, in accordance with aspects of the present approach.
Figure 7:
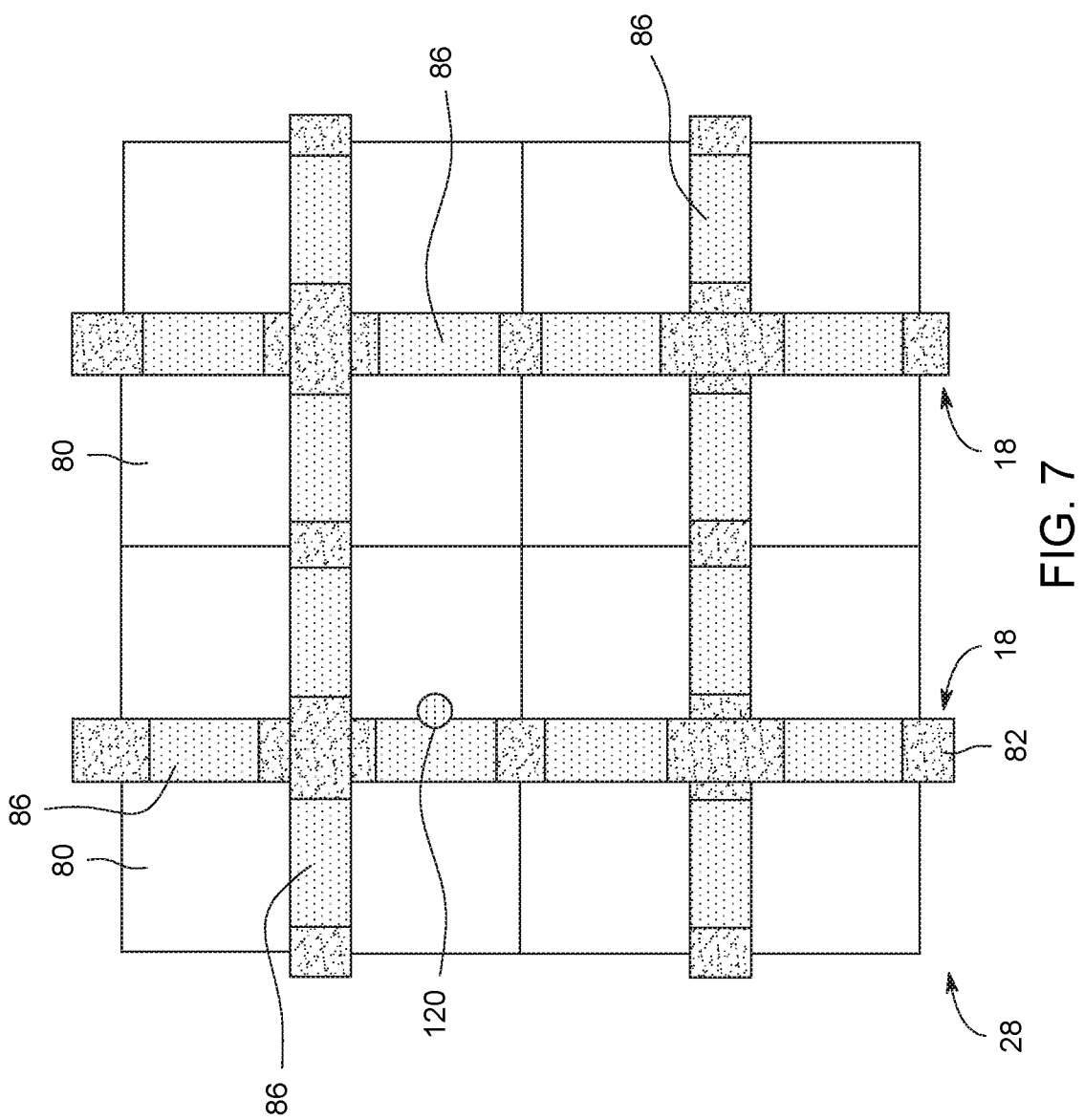
FIG. 7 is a top view of a charge-sharing event in the context of the anti-scatter collimator and detector arrangement of FIG. 3, in accordance with aspects of the present approach.
Figure 8:
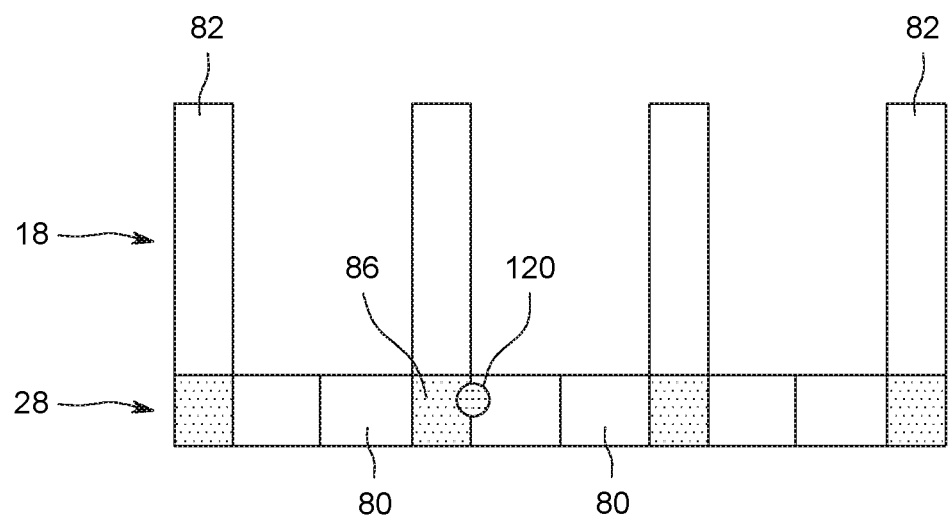
FIG. 8 is a side view of a charge-sharing event in the context of the anti-scatter collimator and detector arrangement of FIG. 4, in accordance with aspects of the present approach.

In another aspect, the use of reference detector pixels 86 situated beneath anti-scatter collimator septa 82 may be used for charge-sharing correction. Charge-sharing events occur when an electron cloud generated in response to an X-ray photon event spans two (or more) adjacent detector pixels, hence sharing the charge from one event between multiple detector pixels. In the present context, each primary pixel 80 is adjacent at least one reference detector pixel 86. As such, a charge-sharing event detected at a reference pixel 86 may be measured and used to correct the measured signal from one or more adjacent primary pixels 80. This is conceptually illustrated in FIGS. 6-8, which respectively depict a top-view of a 1D anti-scatter collimator 18 implementation (FIG. 6), a top-view of a 2D anti-scatter collimator 18 implementation (FIG. 7), and a side-view of an implementation (FIG. 8). In each figure, an electron cloud 120, resulting from the interaction of the X-ray photon with the direct-conversion sensor material, is depicted as spanning a primary pixel 80 and reference pixel 86.

Figure 9:
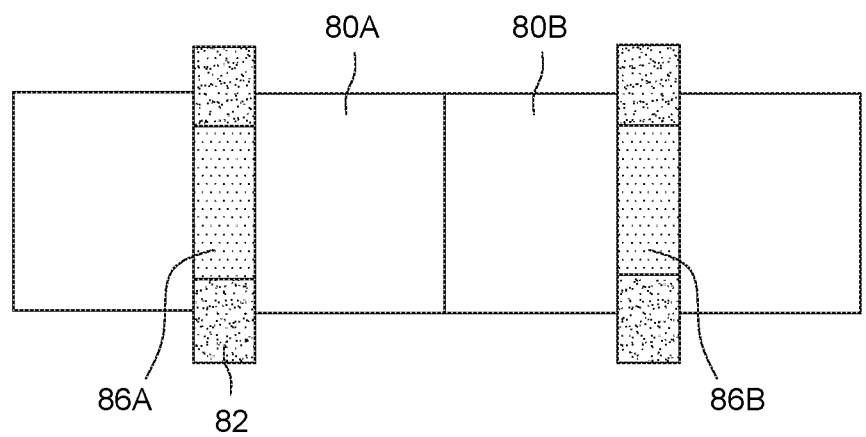
FIG. 9 is a top view of a 1D anti-scatter collimator and detector arrangement with reference detector pixels positioned under the anti-scatter collimator, in accordance with aspects of the present approach.

By way of example, and turning to FIG. 9, a simplified example based on a top-view of a 1D anti-scatter collimator 18 is shown. In this example, the detector 28 includes a first reference pixel 86A adjacent a first primary pixel 80A. The first primary pixel, on the opposite side, is adjacent a second primary pixel 80B which in turn, on the opposite side, is adjacent a second reference pixel 86B. Assuming the incoming X-ray flux is relatively uniform when arriving at the detector 28, for primary pixels 80A and 80B the charge-sharing events correction term should be a weighted summation of the signal from the second reference pixels 86A and 86B.

Figure 10:
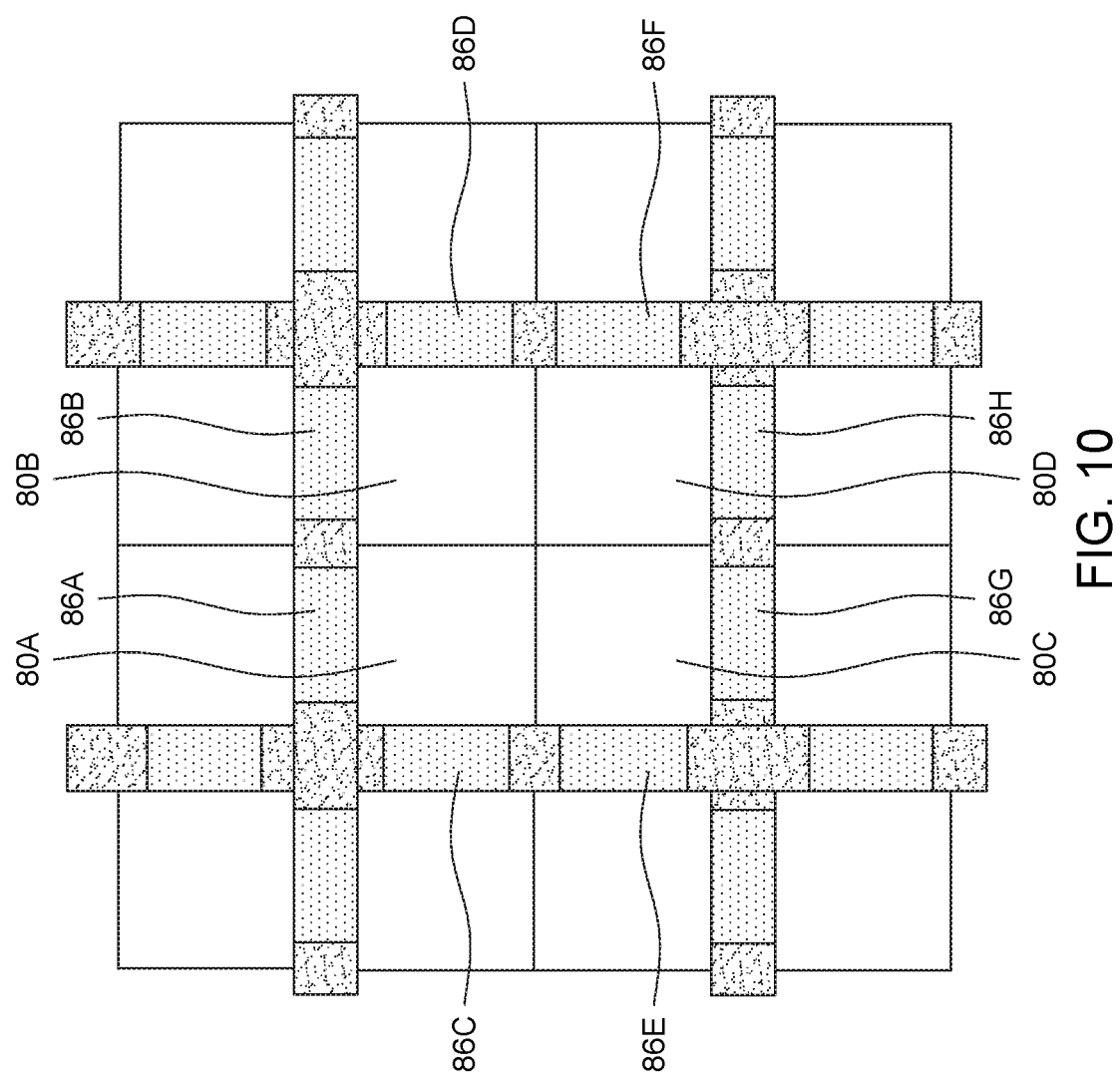
FIG. 10 is a top view of a 2D anti-scatter collimator and detector arrangement with reference detector pixels positioned under the anti-scatter collimator, in accordance with aspects of the present approach.

Turning to FIG. 10, a more complex example corresponding to a 2D anti-scatter collimator example is depicted. In this example, primary pixels 80A, 80B, 80C, and 80D are depicted which are bounded by reference detector pixels 86A, 86B, 86C, 86D, 86E, 86F, 86G, and 86H. In this example: for primary pixel 80A, the charge-sharing correction is a weighted sum of the signal from reference detector pixels 86A, and 86C; for primary pixel 80B, the charge-sharing correction is the sum of the signal from reference detector pixels 86B, and 86D; for primary pixel 80C, the charge-sharing correction is the sum of the signal from reference detector pixels 86E, and 86G; and for primary pixel 80D, the charge-sharing correction is the sum of the signal from reference detector pixels 86F, and 86H.

In certain implementations, more than one reference detector pixel 86 may be provided under a septum segment 130 separating two primary pixels 80. For example, turning to FIG. 11, two side-by-side reference detector pixels 86A and 86B are situated under the same septum segment 130 of the anti-scatter collimator, with one reference detector pixel 86A being positioned proximate to a first primary pixel 80A and the other reference detector pixel 86B being positioned proximate to a second primary pixel 80B. As may be appreciated, from an implementation standpoint, the reference detector pixels 86A and 86B may be provided as physically separate and distinct structures or a common or single structure where the reference pixel operations (e.g., read out and reset) are effectively electrically separated, such as by different portions of a single pixel structure being electrically managed using separate and distinct circuits.

As will be appreciated, in this arrangement, signal generated by reference detector pixel 86A will be primarily attributable to charge-sharing events with the first primary pixel 80A and signal generated by reference detector pixel 86B will be primarily attributable to charge-sharing events with the second primary pixel 80B. Thus, when primary pixel 80A is trigged by an event, the signal from reference detector pixel 86A can be trigged by the same event due to charge-sharing. Therefore, in such an instance, the signal from the reference detector pixel 86A is added to primary pixel 80A before readout. The same process holds for primary pixel 80B and reference detector pixel 86B.

Figure 11:
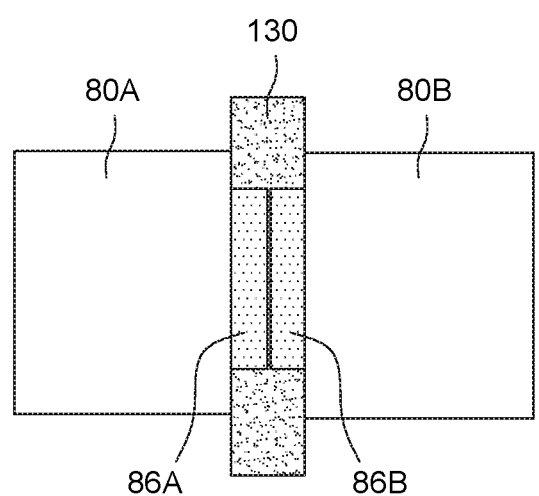
FIG. 11 is a top view of a 1D anti-scatter collimator and detector arrangement with paired or split reference detector pixels positioned under the anti-scatter collimator, in accordance with aspects of the present approach.
Figure 12:
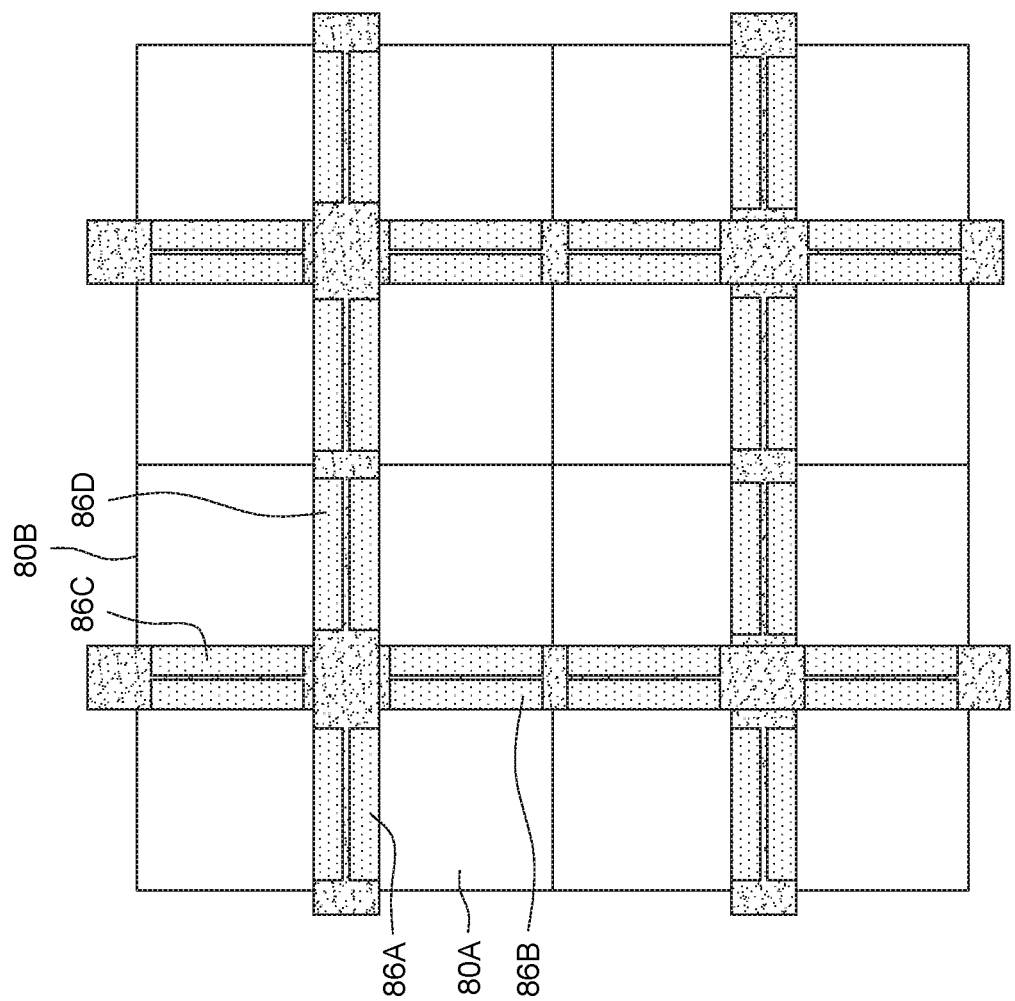
FIG. 12 is a top view of a 2D anti-scatter collimator and detector arrangement with paired or split reference detector pixels positioned under the anti-scatter collimator, in accordance with aspects of the present approach.

As will be appreciated, though the example of FIG. 11 is shown in the context of a 1D anti-scatter grid collimator for simplicity, the same principle can be applied in a 2D anti-scatter grid context. In these contexts, for each primary pixel, the signal from the direct adjacent reference detector pixels are used for charge-sharing correction. For example, in the 2D anti-scatter collimator example of FIG. 12, signal from the reference detector pixels 86A and 86B may be added to the primary pixel 80A before readout in a charge-sharing event. Similarly, signal from the reference detector pixels 86C and 86D may be added to the primary pixel 80B before readout in a charge-sharing event, and so forth.

Figure 13:
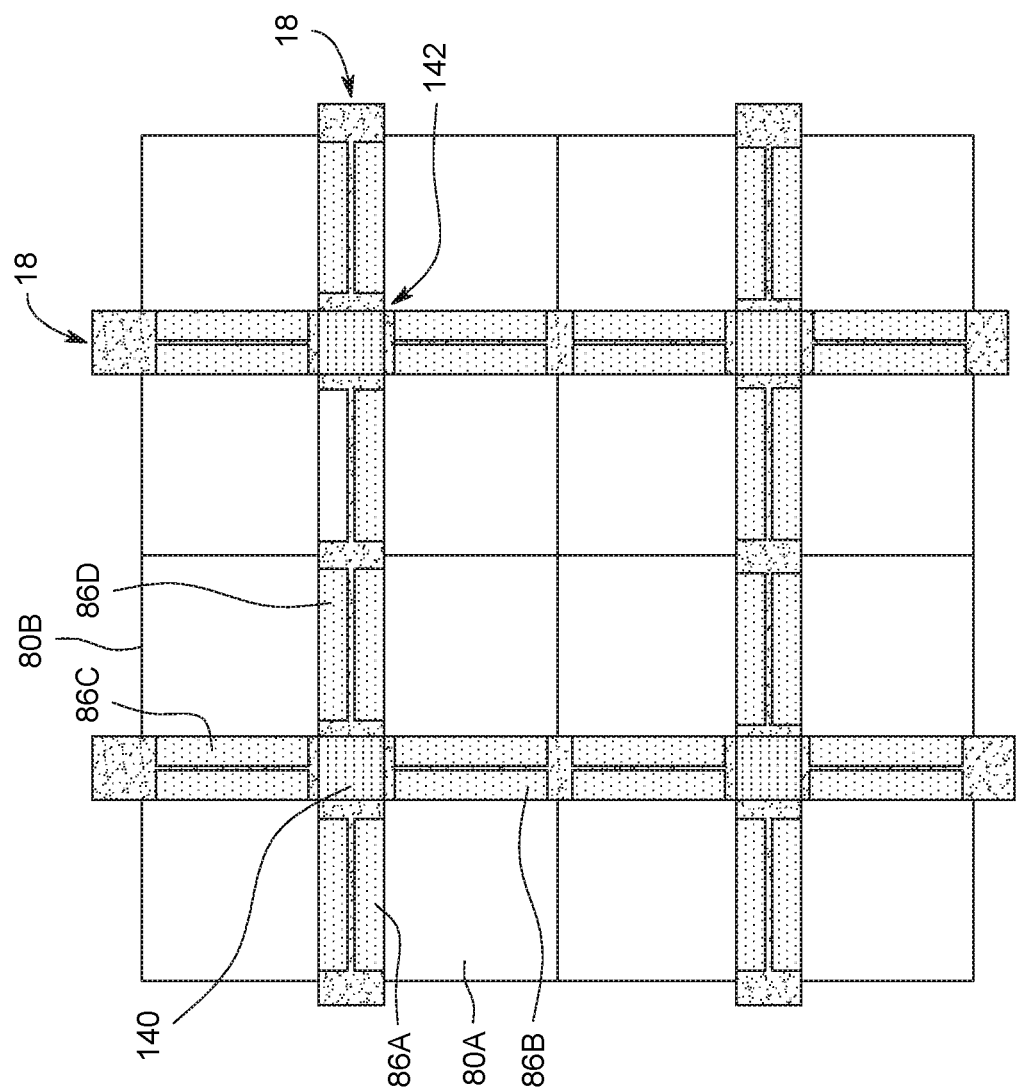
FIG. 13 is a top view of a 2D anti-scatter collimator and detector arrangement with reference detector pixels positioned under the anti-scatter collimator segments and intersections, in accordance with aspects of the present approach.

With the preceding in mind, and turning to FIG. 13, reference detector pixels 140 may also be provided under the septa intersections 142 of a 2D anti-scatter collimator 18. As will be appreciated, such reference detector pixels 140 are actually proximate or adjacent four primary pixels, and thus their signals may be used accordingly. Further, the use of differently positioned reference detector pixels (i.e., reference pixels 86 under septum segments and reference pixels 140 under septa intersection) may allow different correction operations to be performed.

By way of example, in one implementation signals acquired from reference detector pixels 86 under the septum segments can be used for charge-sharing correction, as discussed herein. In such an approach, reference detector pixels 140 under the septa intersections can be used for focal spot alignment correction, also as discussed herein. In this manner, both charge-sharing correction and focal spot alignment correction may be simultaneously performed. To distinguish the signal from the charge-sharing events and the signal from the misalignment of the focal spot, the energy information of the signal can be used. Typically, charge-sharing events would result in a signal in the reference detector with low energy. On the other hand, if the primary signal reaches the reference detector from the misalignment of the focal spot, the signal would have higher energy, which may be used as a basis to differentiate such a signal from the charge-sharing signals.

Figure 14:
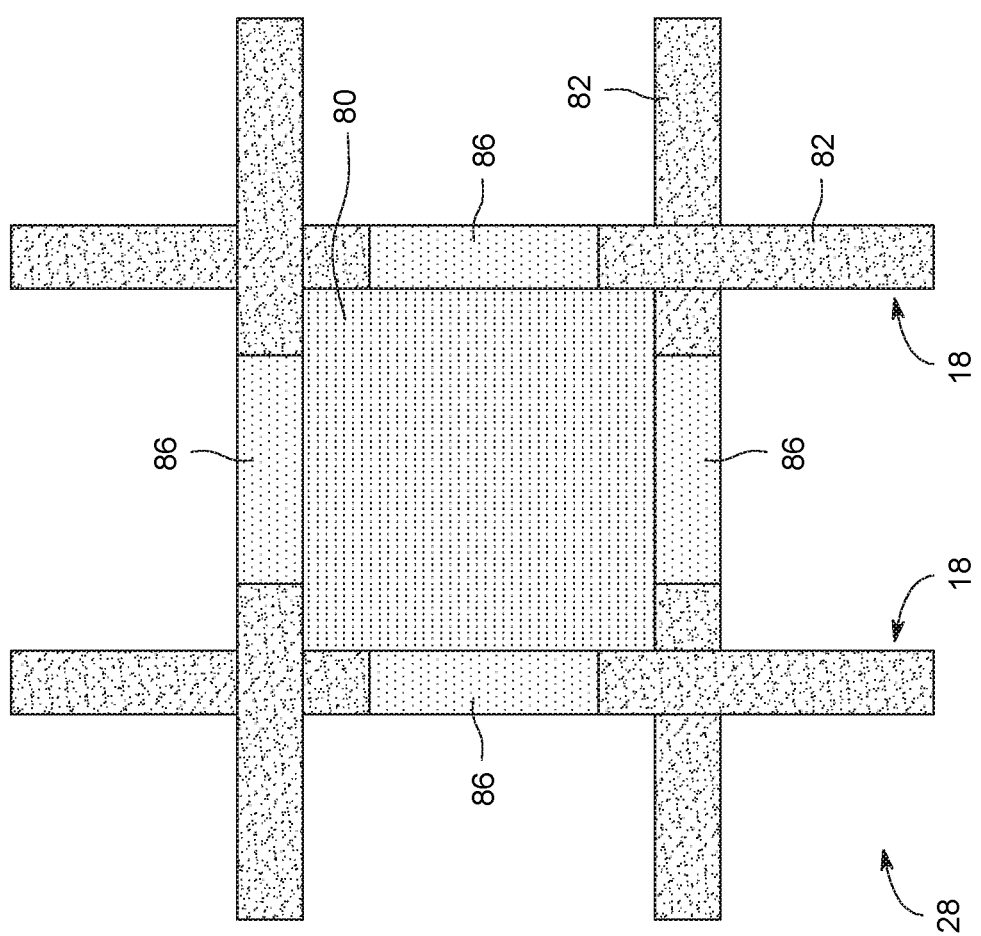
FIG. 14 is a top view of a two-dimensional (2D) anti-scatter collimator and detector arrangement with reference detector pixels positioned under the anti-scatter collimator, in accordance with aspects of the present approach.
Figure 15:
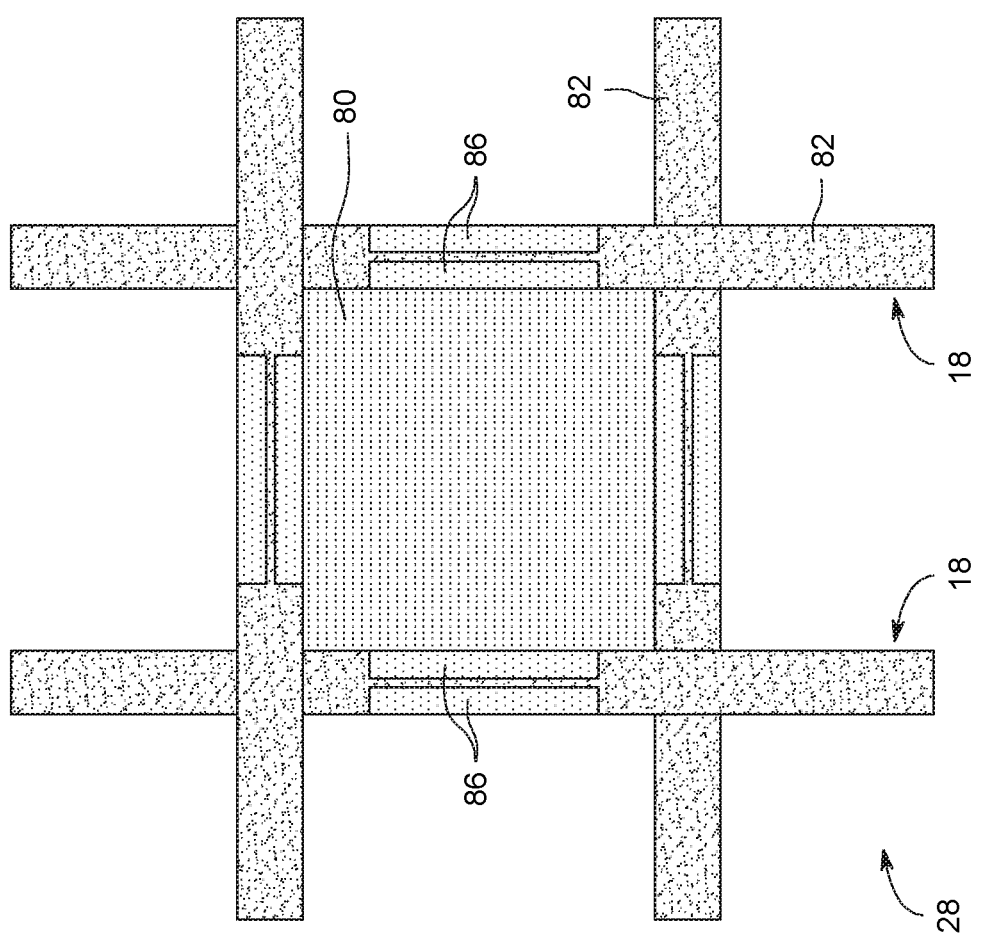
FIG. 15 is a top view of a 2D anti-scatter collimator and detector arrangement with paired or split reference detector pixels positioned under the anti-scatter collimator, in accordance with aspects of the present approach.

In addition, it should be appreciated that though the preceding examples depict septa 82 (and thereby reference pixels 86) positioned around groups or arrays of active pixels 80 (e.g., 2×1, 2×2, 4×4 arrays or other configurations), in other implementations each active pixel 80 may be enclosed by septa 82, as shown in FIGS. 14 and 15. In the depicted examples of FIGS. 14 and 15, the anti-scatter collimator 18 is a 2D collimator within which each cell of the grid encompasses a single active pixel, such as a 500 μm×500 nm detector pixel. FIG. 14 depicts an example in which each active pixel 80 is surrounded on all sides by septa 82, and thus has reference pixels 86 on all sides. Similarly, FIG. 15 depicts a corresponding example in which, instead of a single reference pixel 86 beneath each septum 82 adjacent an active pixel 80, pairs of side-by-side reference pixels 86 may instead be provided, such that each active pixel 80 is surrounded by reference pixels 86 associated only with active pixel 80 in question.

Technical effects of the invention include the use of detector elements (i.e., reference detector pixels) positioned under septa of an anti-scatter collimator as a reference detector, such as for use with a room-temperature semiconductor detector system (e.g., a direct-conversion detector). Since the reference detector pixels are under the anti-scatter collimator, the primary signal incident thereupon is blocked in normal operation. Thus, signal detected by the reference detector pixels typically comes from charge-sharing events, assuming the X-ray focal spot is properly aligned. In this context, the signal generated by the reference detector pixels can be used to correct for charge-sharing events from neighboring primary pixels.

In addition, the signal from the reference detector pixels is sensitive to relative motion between the X-ray focal spot and the detector. This relationship can be used to calibrate the relative position of the collimator and the X-ray source or to adjust the position of the focal spot in real-time based on direct feedback of the signals from the reference detector. These aspects are important for obtaining high-fidelity signals from a direct-conversion detector system, thereby enhancing image quality.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A radiation detector assembly, comprising:
   an anti-scatter collimator comprising X-ray attenuating septa arranged in a one-dimensional or two-dimensional geometry;
   a radiation detector panel, comprising:
      an array of primary pixels positioned so as to not be beneath the septa of the anti-scatter collimator; and
      at least one reference pixel adjacent one or more respective primary pixels and positioned beneath a respective septum or intersection of septa; and
      wherein the at least one reference pixel is smaller in area than a respective primary pixel.

2. The radiation detector assembly of claim 1, comprising readout electronics configured to combine a signal from the at least one reference pixel and a respective primary pixel when a charge-sharing event occurs.

3. The radiation detector assembly of claim 1, wherein the at least one reference pixel comprises a plurality of reference pixels disposed beneath one or more of the septa or septa intersections.

4. The radiation detector assembly of claim 1, wherein the at least one reference pixel comprises a plurality of reference pixels, wherein each reference pixel is adjacent to at least one primary pixel.

5. The radiation detector assembly of claim 1, wherein the at least one reference pixel comprises a plurality of reference pixels, and wherein the plurality of reference pixels is arranged in pairs beneath at least a portion of the X-ray attenuating septa such that a first reference pixel of a pair is adjacent to a first primary pixel while a second reference pixel of a pair is adjacent to a second primary pixel.

6. The radiation detector assembly of claim 1, wherein the radiation detector panel is a direct-conversion detector panel.

7. A method for X-ray signal correction, comprising:
   reading out signals from a plurality of primary pixels, wherein the plurality of primary pixels is positioned so as to not be beneath X-ray attenuating septa or septa intersections of an anti-scatter collimator positioned proximate to a detector panel;
   reading out signals from at least one reference pixel adjacent one or more respective primary pixels, wherein the at least one reference pixel is positioned beneath X-ray attenuating septa or septa intersections of the anti-scatter collimator positioned proximate to the detector panel;
   analyzing the signals for an indication of one or both of a charge-sharing event or an X-ray focal spot misalignment;
   based on the analysis, performing a correction for one or both of the charge-sharing event or X-ray focal spot misalignment; and
   wherein the at least one reference pixel is smaller in area than a respective primary pixel.

8. The method of claim 7, wherein analyzing the signals comprises analyzing the signals for a signal pattern indicative of X-ray focal spot misalignment; and further comprising:
   if no signal pattern is detected, taking no corrective action; and
   if a signal pattern is detected, estimating an X-ray focal spot position based on the signal pattern.

9. The method of claim 7, wherein reading out the at least one reference pixel is performed during an air scan and further comprising:
   generating a calibration factor correcting for misalignment of the X-ray focal spot;
   using the calibration factor to adjust data read out from the plurality of primary pixels of the detector panel in subsequent readout operations to compensate for X-ray focal spot misalignment, wherein the subsequent readout operations are scans of an object or patient; and
   using the calibration factor to adjust the position of focal spot in real time to compensate for the misalignment.

10. The method of claim 7, further comprising:
    calculating adjustments for X-ray focal spot misalignment observed during a scan; and
    using the adjustments for focal spot misalignment during an image reconstruction.

11. The method of claim 7, wherein reading out the at least one reference pixel comprises reading out the at least one reference pixel on at least one edge of the detector panel.

12. The method of claim 7, wherein the at least one reference pixel is read out separately from a plurality of primary pixels.

13. The method of claim 7, wherein analyzing the signals comprises analyzing the signals for a charge-sharing event; and further comprising:
    generating one or more respective charge-sharing signals to correct for the charge-sharing event for one or more respective primary pixels adjacent to the respective reference pixel for which the charge-sharing event was detected.

14. An imaging system, comprising:
    an X-ray source configured to emit X-ray photons from a focal spot during operation;
    a radiation detector assembly, comprising:
       an anti-scatter collimator comprising X-ray attenuating septa; and
       a radiation detector panel, comprising:
          an array of primary pixels positioned so as to not be beneath the septa of the anti-scatter collimator; and
          at least one reference pixel positioned beneath respective septa or intersections of septa;
       readout electronics configured to combine a signal from the at least one reference pixel and a respective primary pixel when a charge-sharing event occurs;
       wherein the at least one reference pixel is smaller in area than a respective primary pixel.

15. The imaging system of claim 14, wherein the radiation detector panel is a direct-conversion detector panel.

16. The imaging system of claim 14, further comprising a processing component configured to analyze signals read out from the at least one reference pixel for a signal pattern and to estimate an X-ray focal spot position based on the signal pattern when detected.

17. The imaging system of claim 16, wherein the processing component is further configured to:
    generate a calibration factor correcting for misalignment of the focal spot;
    use the calibration factor to adjust data read out from the array of primary pixels in subsequent readout operations to compensate for focal spot misalignment; and
    use the data adjusted focal spot misalignment during an image reconstruction.

18. The imaging system of claim 16, wherein the processing component is further configured to:
    calculate adjustments for focal spot misalignment observed during a scan; and
    provide feedback to adjust the position of the focal spot in real-time.

19. The imaging system of claim 16, wherein the processing component is further configured to:
    calculate adjustment factors for focal spot misalignment observed during a scan, and
    use the adjustment factors during an image reconstruction.

* * * * *